United States Patent [19]

Desjardins

[11] Patent Number: 4,738,369

[45] Date of Patent: Apr. 19, 1988

[54] CEILING SUPPORT FOR PATIENT MONITORING EQUIPMENT

[76] Inventor: Wallace H. Desjardins, 352 Lake Blvd., Lindenwold, N.J. 08021

[21] Appl. No.: 873,259

[22] Filed: Jun. 6, 1986

Related U.S. Application Data

[63] Continuation of Ser. No. 520,805, Aug. 5, 1983, abandoned.

[51] Int. Cl.$^4$ .............................................. A47F 5/08
[52] U.S. Cl. .................... 211/113; 211/94; 211/162; 211/117; 211/208; 248/318; 248/333
[58] Field of Search ................ 211/94, 94.5, 113, 117, 211/115, 162, 208, 122, 151, 131, 144, 166; 248/318, 230, 333; 104/95, 109; 105/154

[56] References Cited

U.S. PATENT DOCUMENTS

| | | | |
|---|---|---|---|
| 495,409 | 4/1893 | Fry | 211/115 |
| 688,674 | 12/1901 | Oehmen | 211/115 |
| 691,086 | 1/1902 | Valley | 104/109 |
| 740,182 | 9/1903 | Rood | 248/230 |
| 1,065,381 | 6/1913 | Martin | 211/166 X |
| 1,237,860 | 8/1917 | Beausejour | 211/115 X |
| 1,572,941 | 2/1926 | McBride | 104/95 X |
| 1,637,688 | 8/1927 | Emel | 211/117 |
| 2,782,937 | 2/1957 | Schlissel | 211/166 |
| 2,980,261 | 4/1961 | Young, Jr. | 211/166 X |
| 3,006,481 | 10/1961 | Gussack | 211/117 |
| 3,101,678 | 8/1963 | Grube | 104/95 |
| 3,321,090 | 5/1967 | Greenstadt | 211/162 |
| 3,579,938 | 5/1971 | Hanson | 248/230 X |
| 3,642,241 | 2/1972 | Kaufman | 211/117 X |
| 3,691,961 | 9/1972 | Zeldman et al. | 104/95 X |
| 3,814,023 | 6/1974 | Stantial | 105/154 X |
| 4,047,687 | 9/1977 | Turner | 211/117 X |
| 4,289,076 | 9/1981 | Miller | 104/95 X |
| 4,289,244 | 9/1981 | Frankhouser et al. | 211/117 |

FOREIGN PATENT DOCUMENTS 566504 9/1957 Italy ..................................... 211/151

Primary Examiner—Ramon S. Britts
Assistant Examiner—Blair M. Johnson
Attorney, Agent, or Firm—Alexis Barron; Richard D. Weber

[57] ABSTRACT

A support for patient monitoring equipment is provided by a vertical column suspended from a ceiling by a carriage assembly mounted for transverse movement on roller assemblies along a pair of parallel ceiling-mounted tracks. The column is stabilized by the roller assemblies which include rollers bearing on the track flanges as well as rollers disposed beneath the tracks effectively preventing rocking movement of the column. In the preferred embodiment, a rotatable sleeve is disposed on the vertical column for mounting of an infusion pump and permits rotation of the pump to any desired facing position. A telescoping tube within the column is selectively positionable between upper and lower positions and carries IV bottle mounting arms on its upper end. The arms may be lowered for attachment and removal of the bottles and raised and locked at an elevated operating position.

13 Claims, 2 Drawing Sheets

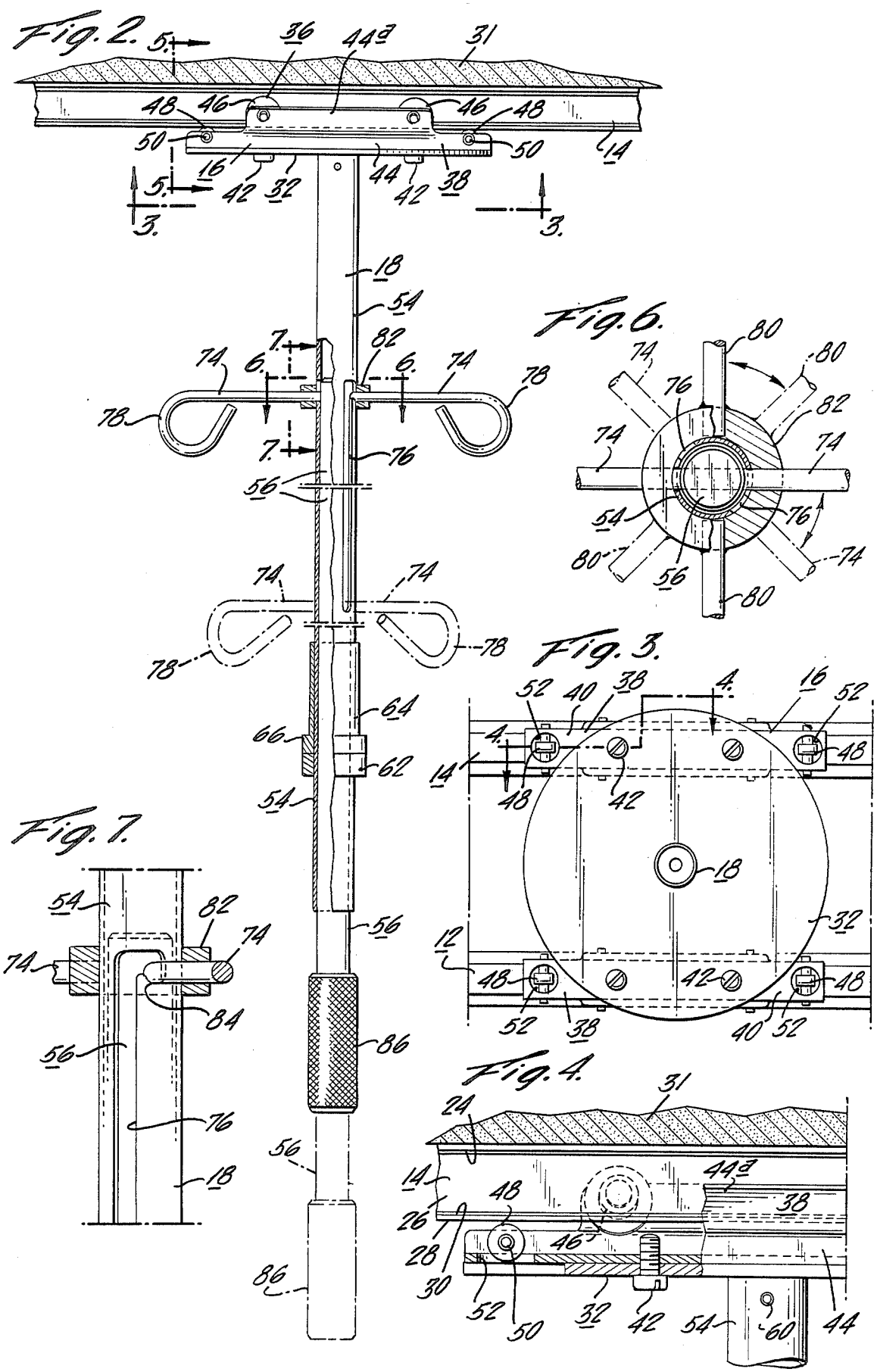

CEILING SUPPORT FOR PATIENT MONITORING EQUIPMENT

This is a continuation of co-pending application Ser. No. 520,805, filed on Aug. 5, 1983, now abandoned.

BACKGROUND OF THE INVENTION

The present invention relates generally to hospital equipment and relates more particularly to a ceiling mounted support for patient monitoring equipment. Although the support may be utilized for a variety of types of equipment, it has been developed primarily for infusion pumps and solution containers.

Infusion pumps for metering and monitoring the flow of intravenous solutions to a hospital patient are widely used. The pumps are conventionally mounted on a portable roller stand which in use is positioned by a patient's bedside. The stand serves to support the solution container above the pump for initial gravity flow of solution to the pump, and further supports the pump at a convenient level for setup and monitoring during use. Since the infusion pumps are fairly heavy, on the order of ten pounds, and since the pump and the solutions together are located at a substantial height above the floor, the stand necessarily requires substantial supporting legs in order to provide the necessary degree of stability. A typical stand includes six legs radiating from the hub, much like the spokes of a wheel.

Although conventional roller-type infusion pump stands serve their intended purpose, they occupy a considerable amount of room in the already crowded area at a patient's bedside. In many cases, a patient requires the use of a number of accessory devices at the same time, most of which are brought into position on roller stands. Because of the substantial width of the stand bases required for stability, the feet of the several stands limit the number of stands which can be placed by a given bedside and in addition, restrict access to the patient.

BRIEF DESCRIPTION OF THE INVENTION.

The present invention provides a ceiling-mounted support for patient monitoring equipment such as an infusion pump which eliminates the need for a floor supported roller stand but still permits the selection of the pump location along the patient's bedside. The present support includes a pair of parallel track members secured to the ceiling of the patient's room, preferably disposed adjacent to and parallel with the edge of the patient's bed. A carriage assembly is connected to the rails by roller assemblies to permit selective linear movement of the carriage along the extent of the rails. A vertical tubular support column is attached at its upper end to the carriage assembly and includes adjacent its lower end a support sleeve for an infusion pump which is rotatably mounted to permit the desired orientation of a pump attached thereto. A plurality of supporting arms on the vertical column are provided for holding bottles of solution. In a preferred embodiment, the bottle support arms are selectively movable from an elevated operating position to a lowered loading position by actuation of an arm level control rod disposed in telescoping relation within the vertical column.

In a preferred embodiment, the invention further includes a novel roller arrangement for providing stability to the suspended pump both during repositioning as well as during stationary operation of the pump.

It is accordingly a first object of the present invention to provide a support for patient monitoring equipment which is suspended from the ceiling, thereby freeing the space therebeneath for other equipment.

A further object of the invention is to provide a ceiling-mounted support as described which includes means permitting selective movement of the support to a desired position.

Another object of the invention is to provide a support as described which provides a rigid, non-swaying support to the equipment while permitting its rotation to facilitate setup and monitoring.

A still further object of the invention is to provide support as described which includes bottle support arms for the suspension of intravenous solutions above the mounting position of the equipment.

Still another object of the invention is to provide a support as described wherein the bottle mounting arms may be readily lowered to a loading position and quickly raised and locked in an elevated operating position.

Still another object of the invention is to provide a support as described of a relatively simple construction which can be economically manufactured and installed.

Additional objects and advantages of the invention will be more readily apparent from the following detailed description of a preferred embodiment thereof.

BRIEF DESCRIPTION OF THE DRAWINGS

FIG. 2 is an enlarged side elevational view of the pump support of FIG. 1 with the vertical column thereof interrupted and partly broken away and in section to show the interior details thereof;

FIG. 3 is a bottom plan view taken along line 3—3 of FIG. 2;

FIG. 4 is an enlarged view partly in section taken along line 4—4 of FIG. 3;

FIG. 6 is an enlarged view taken along line 6—6 of FIG. 2; and

FIG. 7 is an enlarged view taken along line 7—7 of FIG. 2.

DESCRIPTION OF THE PREFERRED EMBODIMENT

Although it should be understood that the invention can be usefully employ to support a variety of types of equipment in a patient's hospital room, in an examination room or operating room or wherever the equipment can be advantageously supported from the ceiling, the principal use for which the invention was developed is the support of an infusion pump and associated solution containers at a patient's bedside, and the preferred embodiment of the invention is accordingly directed to its use as an infusion pump support.

Figure 1:
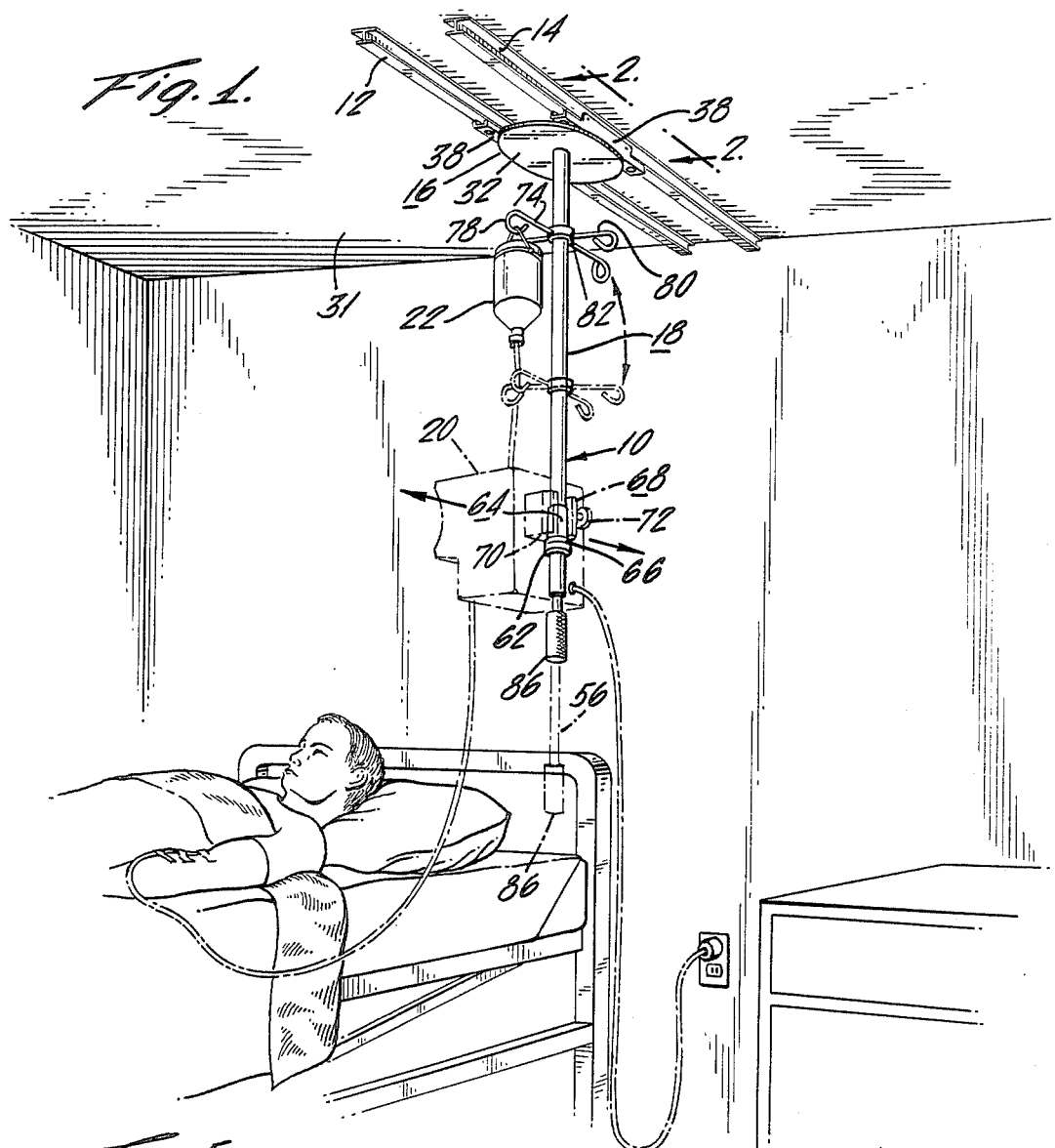
FIG. 1 is a perspective view showing a ceiling mounted support for an infusion pump in accordance with the present invention installed adjacent a patient's bed and showing in dot/dash lines an infusion pump supported thereby for metering the flow of an intravenous solution to a patient.

Referring to the drawings and particularly FIG. 1 thereof, the present infusion pump support generally designated 10 includes as its basic elements, a pair of spaced parallel track members 12 and 14 secured to the ceiling of a patient's room, a carriage assembly 16 provided with roller means cooperating with said tracks, and a vertical column assembly 18 secured to the carriage 16. An infusion pump 20 is shown in broken lines in FIG. 1 clamped to the column assembly 18 adjacent the lower end thereof. The support also includes means for holding solution bottles such as the bottle 22 at a suitable height above the pump.

Figure 5:
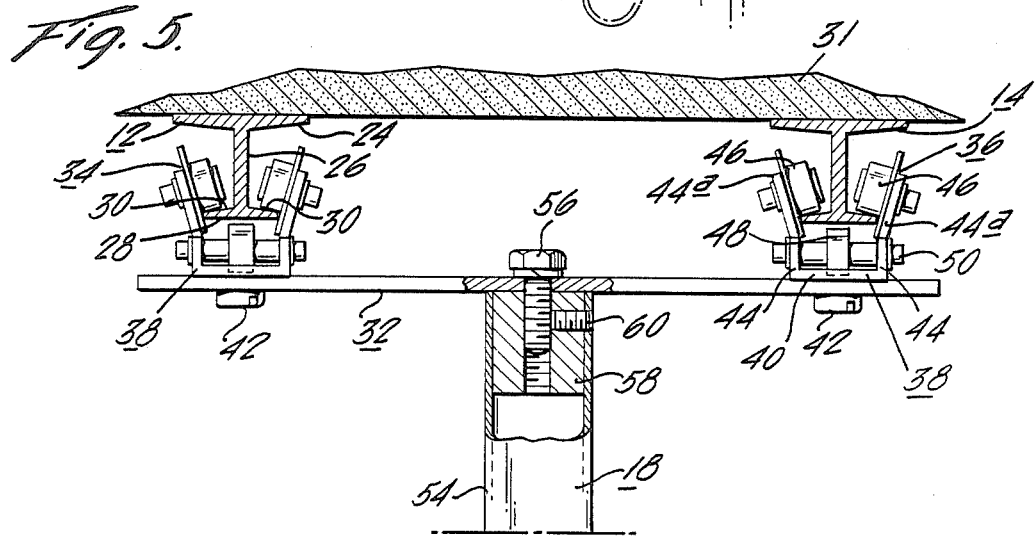
FIG. 5 is an enlarged view taken along line 5—5 of FIG. 2 with a portion thereof broken away and in section to show interior details.

Considering the details of the several components of the support 10, the track members 12 and 14 as shown most clearly in FIG. 5 are of a modified "I-Beam" shape, each track member having a relatively wide upper flange 24, a vertical web 26, and a relatively narrow lower flange 28. The flange 28 of each track presents a pair of upwardly directed flange faces 30 which are inclined slightly from the horizontal and which represents support surfaces for the carriage roller assemblies.

The track elements are secured to the ceiling 31 of the patient's room in spaced parallel relation by means of screws or other suitable fastenings (not shown) extending through the upper flanges 24 into the ceiling. The track members are preferably located on the ceiling over the area adjacent the side of a patient's bed and extending parallel to the side edge of the patient's bed. Cross members extending between the tracks to maintain the parallel relation of the tracks during installation and stop members at the track ends to limit movement of the carriage assembly are advantageous accessories which have not been illustrated.

The carriage assembly 16 comprises a circular carriage plate 32 which, as best shown in FIGS. 3–5 is suspended beneath the track elements 12 and 14 by a pair of roller assemblies 34 and 36 which are of identical construction and the elements of which accordingly bear the same reference numerals. The roller assemblies each include a channel shaped frame 38 having a web portion 40 attached to the plate 32 by screws 42 and a pair of upwardly directed flanges 44. An upper portion 44a of the flanges 44 is bent outwardly from the vertical and supports adjacent each end thereof a pair of rotatably mounted rollers 46. The outward inclination of the flanges 44a provides a proper seating of the rollers on the inclined flange spaces 30 of the tracks. As shown in FIG. 2, the rollers 46 are spaced on opposite sides of and substantially equidistant the transverse plane of the point of attachment of the column 18 to the carriage plate 32.

Although the rollers 46 uniformly carry the weight of the carriage assembly and the column assembly, additional stabilizing rollers are required to maintain the vertical disposition of the column when unbalanced loads are applied thereto or when the column is subjected to lateral forces such as during movement, the attachment and set up of the pump and bottles, or upon accidental engagement therewith. Accordingly, additional stabilizing rollers 48 rotatably disposed on support shafts 50 extending between the flanges 44 of the frame members 38 are provided to engage the bottom surface of the lower track flanges 28 as required to maintain the vertical disposition of the column assembly. Holes 52 are provided in the web portion of the frame members aligned with the rollers 48 to provide clearance for the rollers as shown for example in FIGS. 3 and 4. Increased stability is provided by the location of the rollers 48 longitudinally outboard of the rollers 46 as shown in FIG. 2. The rollers 48 are disposed on opposite sides of and substantially equidistant a transverse plane passing through the center of the vertical column assembly.

The vertical column assembly 18 includes an outer cylindrical tube 54 and an inner cylindrical tube 56 disposed therewithin in telescoping slideable relation thereto. The outer tube 54 is secured to the center of the carriage plate 32 by means of a screw 57 extending through a hole in the carriage plate and passing in threaded relation into an axial bore in a plug 58. The plug 58 is locked to the upper end of the tube 54 by a set screw 60 passing through the tube into the plug.

The outer tube 54 is provided with a pump supporting collar 62 which is secured thereto by a locking screw (not shown) passing therethrough into the outer tube. A pump sleeve 64 having a flange 66 on its lower end is disposed on the outer tube 54 above the collar 62 with the flange 66 thereof in engagement with the collar 62. The sleeve 64 is rotatable on the outer tube 54 and is adapted to receive the clamping mechanism 68 of an infusion pump 20 as shown in FIG. 1. The clamping mechanism 68 typically includes a clamping bracket 70 having a vertically oriented slot therein for receiving a cylindrical element, and a locking screw 72 extending through the bracket and serving, in this instance, to tightly secure the pump to the sleeve 64 with the lower end of the bracket resting on the sleeve flange 66. This mounting arrangement securely holds the pump at a convenient level above the floor and permits it rotation to any desired position for setup or monitoring. By movement of the column and carriage assembly along the tracks the pump may be positioned so as not to interfere with other equipment or the personnel attending the patient.

The means for adjustably supporting IV bottles in an elevated position above the pump comprises a first pair of opposed bottle support arms 74 which extend in diametrically opposed relation from the inner tube 56, extending through parallel diametrically opposed slots 76 in the outer tube 54. The outer ends 78 of the arms 74 are configured in a hook shaped manner to receive the IV bottle hangers.

A second pair of IV bottle arms 80 are attached to a ring 82 carried by the arms 74 and slidable along the exterior of the outer tube 54. The arms 80 are substantially identical to the arms 74 and are disposed at right angles thereto.

As shown in FIG. 7, the slots 76 at their upper ends include offset portions 84 providing locking channels to secure the arms in the elevated position. By manipulation of the handle 86 at the lower end of the inner tube 56, the inner tube and the arms 74 and 80 connected thereto can be selectively moved from the elevated operating position to be lowered position shown in dot/dash lines in FIG. 1 for placement or removal of the bottles. This arrangement greatly facilitates the initial setup of the unit and the servicing of the bottles.

As can be gained rom the foregoing description, the operation of the present device is straightforward. With the tracks 12 and 14 secured to the ceiling of a patient's room, preferably parallel to and above the side edge of a patient's bed, the vertical column 18 is readily accessible and may be moved from a storage position adjacent a wall of the room to an operating position adjacent the patient. The pump 20 is attached to the sleeve 64 by means of the locking screw 72 and is connected with a source of electrical current. By turning the handle 85 in a counterclockwise manner, the inner tube 56 and the attached arms 74 and 80 may be lowered to permit the attachment of one or more IV bottles 22 thereto. The inner tube is then raised to the elevated position with the arms 74 engaged in the locking channels 84. The IV bottle or bottles are then connected with the pump 20 and the pump is connected to the patient in the usual manner for delivery of intravenous solutions. Since the sleeve 64 is rotatable on the outer tube 54, the pump 20 may be faced in any desired direction during the initial setup and for periodic monitoring. Similarly, the column, pump and bottles may be moved along the extent of the tracks 12 and 14 to the most convenient position to permit the placement of other equipment or to gain access to the patient.

The stability of the column is enhanced by arrangement of the rollers and particularly the presence and location of the rollers 48 beneath the tracks and substantially spaced from the column axis.

As indicated above, the present invention may be used with other hospital equipment and in locations other than the patient's room. Operating rooms and emergency rooms require unimpeded access to the patient and conventional floor support roller stands for patient monitoring equipment interfere with such access.

With minor modification, such as the provision of a support shelf at the lower end of the vertical column assembly, the present device can be employed for the support of heart monitors, temperature monitors and other types of equipment heretofore mounted on floor supported stands. The column assembly could comprise a plurality of tubes to provide increased rigidity for supporting heavier apparatus or for supporting multiple units on a single support.

Manifestly, changes in details of construction can be effected by those skilled in the art without departing from the spirit and scope of the invention as defined by the appended claims.

I claim:

1. A support for patient monitoring equipment comprising a track assembly adapted for mounting on a ceiling, said track assembly comprising a pair of parallel spaced track elements, a carriage assembly having means comprising rollers cooperating with said track elements to permit selective movement of said carriage assembly along said track assembly, vertical support means extending downwardly from said carriage assembly, said support means being rigidly attached to said carriage assembly, stabilizing means on said carriage assembly cooperating with said track assembly for maintaining a constant attitude of said carriage assembly and hence a substantially vertical disposition of said support means even under unbalanced load conditions, said stabilizing means comprising means disposed beneath said track elements and engageable with the downwardly facing surfaces thereof, and means at the lower end of said vertical support means for supporting patient monitoring equipment.

2. In combination, an infusion pump, support means for said pump comprising a track assembly adapted for mounting on a ceiling of a hospital room, said track assembly comprising a pair of parallel spaced track elements, a carriage assembly having means comprising rollers cooperating with said track elements to permit selective movement of said carriage assembly along said track assembly, a vertical column extending downwardly from said carriage assembly, said column being rigidly attached to said carriage assembly, stabilizing means on said carriage assembly cooperating with said track assembly for maintaining a constant attitude of said carriage assembly and hence a substantially vertical disposition of said column even under unbalanced load conditions, said stabilizing means comprising means disposed beneath said track elements and engageable with the downwardly facing surfaces thereof, and means on said column for attachment of said infusion pump.

3. The invention as claimed in claim 2, wherein said vertical column comprises a tubular column and wherein said means for attachment of said pump comprises a sleeve rotatably mounted on said tubular column.

4. The invention as claimed in claim 3, including support means located above said sleeve for supporting an IV bottle.

5. The invention as claimed in claim 4, wherein said support means comprises arms extending substantially horizontally from said tubular column.

6. The invention as claimed in claim 5, including an inner member disposed in telescoping relation within said tubular column and connected with said arms, said arms extending through slots in said tubular column, the position of said arms being vertically adjustable by movement of said inner member.

7. the invention as claimed in claim 6, including means for locking said arms in an elevated position.

8. An infusion pump support comprising a track assembly adapted for mounting on a ceiling of a hospital room, said track assembly comprising a pair of spaced track elements, each said track element having an upwardly facing flange surface and a downwardly facing flange surface, a carriage assembly disposed for movement along said tracks, said carriage assembly including a roller assembly engaging each said track element, each said roller assembly including spaced rollers engaging said upwardly facing flange surface and spaced rollers engageable with said downwardly facing flange surface, a vertical column rigidly attached to said carriage assembly and extending downwardly therefrom, said vertical column comprising inner and outer cylindrical tubes, a sleeve rotatably mounted on said outer column for receiving and supporting an infusion pump, a longitudinal slot in said outer tube, an arm for supporting an IV bottle attached to said inner tube near the upper end thereof and extending through said slot, a handle portion of said inner tube extending below said outer tube for raising and lowering said inner tube, and means for locking said inner tube and arm in an elevated position.

9. The invention as claimed in claim 8, wherein said outer tube includes a pair of diametrically opposed slots and wherein said inner tube includes a pair of diametrically opposed arms extending from the upper end thereof through said slots.

10. The invention as claimed in claim 9, including a ring attached to said arms and adapted for sliding movement along the exterior of said outer tube, and a second pair of diametrically opposed bottle carrying arms attached to said ring in perpendicular relation to the arms attached to said inner tube.

11. The invention as claimed in claim 8, wherein said sleeve for supporting said pump includes an annular flange at the lower end thereof.

12. The invention as claimed in claim 8, wherein the rollers of each said roller assembly are spaced equidistant from a transverse plane passing through the axis of said column.

13. An infusion pump support comprising a track assembly adapted for mounting on a ceiling of a hospital room, said track assembly comprising a pair of spaced track elements, each said track element having an upwardly facing flange surface and a downwardly facing flange surface, a carriage assembly disposed for movement along said tracks, said carriage assembly including a roller assembly engaging each said track element, each said roller assembly including spaced rollers engageable with said upwardly facing flange surface and spaced rollers engageable with said downwardly facing flange surface, a vertical column extending downwardly from said carriage assembly, said column being rigidly attached to said carriage assembly, said roller assemblies maintaining a constant attitude of said carriage assembly and hence a substantially vertical disposition of said column even under unbalanced load conditions, and means on said column for attachment of an infusion pump.

* * * * *